United States Patent [19]

Rutzen et al.

[11] 4,421,932

[45] Dec. 20, 1983

[54] MANUFACTURE OF QUATERNARY AMMONIUM COMPOUNDS

[75] Inventors: Horst Rutzen, Langenfeld; Manfred Petzold, Duesseldorf-Holthausen, both of Fed. Rep. of Germany

[73] Assignee: Henkel KGaA, Duesseldorf, Fed. Rep. of Germany

[21] Appl. No.: 369,810

[22] Filed: Apr. 19, 1982

[30] Foreign Application Priority Data

Sep. 15, 1981 [DE] Fed. Rep. of Germany ....... 3136564

[51] Int. Cl.³ ............................................ C07C 89/00
[52] U.S. Cl. .................................. 564/292; 564/285; 564/296; 564/294
[58] Field of Search ............... 564/292, 294, 295, 285, 564/2

[56] References Cited

U.S. PATENT DOCUMENTS 3,104,933  9/1963  Mendelsohn et al. .............. 564/292
3,872,116  3/1975  Gipson ................................ 564/292

FOREIGN PATENT DOCUMENTS 704014  2/1954  United Kingdom ................ 564/285

OTHER PUBLICATIONS

Mamaev et al., J. Org. Chem., U.S.S.R., vol. 2, pp. 584–587 (1966).
Stein et al., Chem. Abst., vol. 87, #41080r (1977).
Schonfeldt, "Surface Active Ethylene Oxide Adducts", pp. 669–676 (1970).
J. Goerdeler in Houben–Weyl, Methoden der Organischer Chemie, 4th Edition, vol. 11/12, pp. 592 et seq.

*Primary Examiner*—James H. Reamer
*Attorney, Agent, or Firm*—Ernest G. Szoke; Henry E. Millson, Jr.

[57] ABSTRACT

Process for the manufacture of quaternary ammonium compounds by reacting a compound having a terminal epoxy group with a tertiary amine which is partly present as the free amine and partly present in the form of a salt, followed by the addition of sufficient acid at the end of the reaction to complete salt formation of the quaternary ammonium compound.

10 Claims, No Drawings

MANUFACTURE OF QUATERNARY AMMONIUM COMPOUNDS

BACKGROUND OF THE INVENTION

The manufacture of quaternary ammonium compounds is generally carried out by alkylating a tertiary amine to the quaternary stage. The alkylating agent is usually an ester of a strong mineral acid, especially sulfuric or sulfonic acid esters, or an alkyl halide, for reaction with the tertiary amine. Occasionally, other esters are employed. Another known method for alkylating tertiary amines is by reacting alkylene oxides with tertiary amines in the presence of water. A number of other procedures can also be employed to manufacture quaternary ammonium compounds from readily available teriary amines. See, e.g. J. Goerdeler in Houben-Weyl, Methoden der organischer Chemie, 4th Edition, Vol. 11/12, page 592 et seg.

Quaternary ammonium compounds with one or more long, aliphatic radicals, or one long aliphatic radical and one aromatic radical exhibit antimicrobial as well as textile softening and antistatic properties, and they are used extensively for these purposes. Such compounds are obtained either by alkylating tertiary amines having long aliphatic groups and/or aromatic groups, or by alkylating with alkylating agents that contain long aliphatic or aromatic groups. Obviously, the tertiary amine as well as the alkylating agent can each contain long aliphatic and/or aromatic groups.

Disadvantages of these known processes for the manufacture of quaternary ammonium compounds include the fact that usually pressure must be used, and occasionally solvents are also required. In addition, the yield is usually disappointing.

DETAILED DESCRIPTION OF THE INVENTION

A process has now been discovered for the preparation of quaternary ammonium compounds using terminal epoxides and tertiary amines which does not suffer from the disadvantages of the above prior art processes.

The present process is carried out by reacting a compound having a terminal epoxy group with a tertiary amine which is partly present as the free amine and partly present in the form of a salt, and upon completion of the reaction, sufficient acid is added to the reaction mixture to complete salt formation of the quaternary ammonium compound formed by the reaction.

Partial salt formation of the tertiary amine can be achieved by either of two methods:

(a) Partially converting a 1 amine equivalent into a salt thereof with less than 1 acid equivalent in an aqueous medium. The solution containing the reaction product is then reacted with 1 equivalent of the epoxy compound; or (b) reacting 1 acid equivalent with more than 1 amine equivalent in an aqueous medium. This resulting aqueous solution containing the reaction product is then reacted with 1 equivalent of the epoxy compound.

In both of the above process variants, despite the fact that a two phase reaction mixture is present, the quaternary reaction takes place rather quickly, resulting in a homogeneous reaction mixture. The stochiometrically required remaining quantity of acid, calculated on the basis of complete salt formation of the amines present, is added to the reaction mixture at or close to the end of the reaction. Since in the case of process variant (b) an appreciable quantity of unquaternized amine salt will be present in the reaction mixture, which may be an undesirable contaminant, process variant (a) is preferred.

The mixture consisting of amine and amine salt produced by either process variant, which is used for the reaction with the epoxy compound, should as stated above be present as a solution in water prior to use. Hence, while an anhydrous mixture of amine and amine salt may be used, the anhydrous mixture should be dissolved in water prior to reaction with the epoxy compound.

The reaction between the epoxy compound and the amine salt solution is carried out at a temperature in the range of from about 40° to about 100° C., preferably about 80° to about 95° C.

The extent of salt formation of the amine for use in the present process is from about 50 to about 90 mole %, preferably about 60 to about 80 mole %. Accordingly, the quantity of acid added at the end of the reaction to complete salt formation is in the range of about 50 to about 10 mole %, preferably about 40 to about 20 mole % of the stochiometric amount of acid.

In order to avoid excess quantities of unquaternized salt of the tertiary amine in the reaction mixture, the starting reaction mixture preferably consists of a mixture of 1 epoxide equivalent, 1 amine equivalent, and from about 0.5 to about 0.9, preferably about 0.6 to about 0.8 acid equivalent. At the end of the reaction, which end point can be readily determined by determining the epoxide content of the reaction mixture, from about 0.5 to about 0.1, preferably about 0.4 to about 0.2 acid equivalents are added thereto, i.e. sufficient additional acid to total 1 acid equivalent.

Terminal epoxy compounds for use in the practice of the invention are straight or branched chain 1,2-epoxyalkanes, which are conveniently obtained from the appropriate 1,2-monoolefin or olefin mixture by known methods, such as by the polymerization of ethylene using organic aluminum compounds as catalysts, or by thermal cracking of paraffin hydrocarbons. Examples of preferred 1,2-epoxyalkanes are 1,2-epoxyhexane, 1,2-epoxydecane, 1,2-epoxydodecane, 1,2-epoxytetradecane, 1,2-epoxyhexadecane, and 1,2-epoxyoctadecane. Also suitable are epoxide mixtures such as $C_{12/14}$-1,2-epoxide with about 70 weight percent $C_{12}$- and about 30 weight percent $C_{14}$-epoxyalkane or $C_{16/18}$-1,2-epoxide with about 40 weight percent $C_{16}$- and about 60 weight percent $C_{18}$-epoxyalkane. In addition, a diepoxyalkane having 8 to 20 carbon atoms and two terminal epoxy groups can also be used, such as 1,2-7,8-diepoxyoctane, 1,2-9,10-diepoxydecane, and similar compounds. Also, mono-or di-glycide ethers such as hexadecyl monoglycide ether and 1,4-butanediol-diglycide ether are useful epoxide compounds having terminal epoxide groups. The preferred epoxide compounds that can be employed are either (a) those of the general formula:

(I)

wherein $R^1$ is either a straight or branched chain aliphatic hydrocarbon group having 1 to 21 carbon atoms, preferably 4 to 16 carbon atoms, or a group of the general formula:

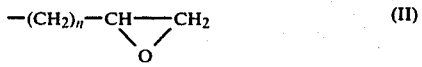

(II)

wherein n is an integer of from 4 to 16; or (b) glycide ethers of the general formula:

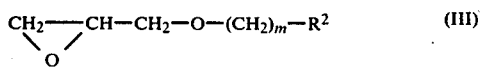

(III)

wherein m is an integer of from 1 to 10, and $R^2$ is hydrogen, or an aliphatic straight or branched chain hydrocarbon group having from 1 to 24 carbon atoms, or a group of the formula:

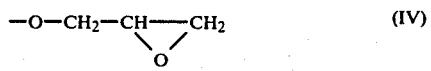

(IV)

Tertiary amines which are suitable (in the form of a partial salt) as reactants with the epoxy compounds used in the process of the invention are the more strongly basic tertiary amines, e.g. those having one or more straight or branched chain alkyl, hydroxyalkyl, or aralkyl (e.g. benzyl, phenylethyl, etc.) groups, or an N-heterocyclic group containing the nitrogen atom of the tertiary amine in the ring structure, wherein such groups contain less than 10 carbon atoms, and wherein the tertiary amine can optionally contain a $C_{10}$ to $C_{20}$ straight or branched chain alkyl or alkenyl group. Examples of such tertiary amines include the trialkylamines, e.g. trimethylamine, triethylamine, tributylamine, dimethylhexylamine, dimethyllaurylamine; the dialkylaralkyl amines, e.g. dimethylbenzylamine; tertiary amines containing one or more hydroxyalkyl groups, e.g. dimethylethanolamine, dimethylpropanolamine, N-$\beta$-hydroxydecyl-N-$\beta$-hydroxyethyl-N-methylamine, N-$\beta$-hydroxyhexadecyl-N-$\beta$-hydroxyethyl-N-methylamine, methyldiethanolamine, dimethylaminopropanediol; tertiary diamines such as tetramethylethylenediamine, or tetramethylpropylenediamine-1,3; and, additionally, heterocyclic tertiary amines having the nitrogen atom in the ring structure, e.g. pyridine, picoline, pipecoline, N-methylpiperidine, N-methylpyrrolidine, quinuclidine, etc.

For the acid component of the amine salt, the following inorganic acids are suitable: hydrochloric acid, sulfuric acid, nitric acid, phosphoric acid, hydrobromic acid, hydriodic acid, hydrofluoric acid, boric acid, carbonic acid, or acid salts such as sodium hydrogen sulfate, or sodium hydrogen phosphate. In addition, the acid component can also be one or more organic acids, such as formic acid, acetic acid, succinic acid, benzoic acid, phosphonic acid, 1-hydroxyethane-1,1-diphosphonic acid, amino-tris(methylenephosphonic acid), phosphoric acid, toluene sulfonic acid, amidosulfonic acid, an alkyl sulfuric acid, 2-phosphonobutane-1,2,4-tricarboxylic acid, or phosphinic acid. Amphoteric compounds such as dimethylaminoacetic acid can also be used.

The process of the invention differs from present state-of-the-art processes in that it does not require pressures in excess of atmospheric, and the reaction takes place at relatively low reaction temperatures and shorter reaction times. In addition, good yields and end products of high purity are obtained.

The reaction products of the present process are useful as textile softeners, anti-static agents, and/or as antibacterial agents for application to surfaces to be disinfected such as containers used in the food industry.

Particularly useful antibacterial products can be obtained from the process of the invention by either (a) reacting an epoxy compound (with or without an ether linkage) having from 10 to 20 carbon atoms with a salt of a tertiary amine having one or more alkyl, hydroxyalkyl or aralkyl groups wherein each group contains fewer than 10 carbon atoms, or (b) reacting an epoxy compound (with or without an ether linkage) having fewer than 10 carbon atoms with a tertiary amine containing a $C_{10}$ to $C_{20}$ alkyl or alkenyl group.

Quaternary ammonium compounds having excellent anti-static and/or textile softening properties can be obtained from the process of the invention by reacting an epoxy compound (with or without an ether group) having at least 6 carbon atoms with a tertiary amine having a $C_{10}$ to $C_{20}$ alkyl or alkenyl group. It has been found that as the number and chain length of the long chain alkyl or alkenyl group increases, the reaction products exhibit gradually increasing textile softening and anti-static properties. Accordingly, the most preferred compounds for these utilities are those formed by the reaction between a tertiary amine that contains a $C_{10}$ to $C_{20}$ alkyl or alkenyl group with an epoxy compound (with or without an ether linkage) having 10 to 20 carbon atoms to produce a quaternary ammonium compound having a $C_{10}$-$C_{20}$ alkyl or alkenyl group, and a $C_{10}$-$C_{20}$ hydroxyalkyl or hydroxyalkylether group.

The use of the above products as textile softeners can be in liquid products such as liquids for the after-treatment of clean laundry. Such liquids may contain, in addition to one or more of the above products, carrier substances, solvents, diluents, emulsifiers, coloring agents, perfumes, preservatives, viscosity modifiers, thickening agents, and/or other commonly used additives.

An example of a composition useful as a laundry after-treatment is as follows:

2—80 wt. % of a quaternary ammonium compound prepared by the process of the invention which has a $C_{10}$-$C_{20}$ hydroxyalkyl or hydroxyalkylether group.

20—98 wt. % of carriers, solvents and/or diluents.

0—20 wt. % emulsifier

0—3 wt. % preservative

0—5 wt. % perfume

0—1 wt. % coloring agent

Also, the quaternary ammonium compounds produced by the process of the invention can be added to detergent formulations which contain at least one laundry-active compound to produce a softening effect on the laundry. Such detergent formulations are usually based on formulations containing nonionic surfactants. Furthermore, the products of the invention can be applied to textile surfaces as an aid in tumbling.

The invention will be better understood from the following examples which are given for illustration purposes only and not to limit the invention.

EXAMPLE 1

44.57 G (0.5 mole) of dimethylethanolamine was diluted in 309.19 g of water, and 39.44 g (0.5 mole) of 37% HCl was added thereto. 94.0 G (0.5 mole) of 1,2-epoxydodecane (epoxide number 8.51) was added to the mixture at 95° C., and the resulting mixture stirred at that temperature for 6 hours. The epoxide number was then 0.01. Lastly, 9.86 g (0.1 mole) of 37% HCl was added. The clear solution contained 97.3% of the theoretically possible amount of quaternary ammonium compound.

EXAMPLE 2

44.57 G (0.5 mole) of dimethylethanolamine was diluted in 309.19 g of water, and then mixed with 29.58 g (0.3 mole) of 37% HCl. 94.0 G (0.5 mole) of 1,2-epoxydodecane (epoxide number 8.51) was added thereto at 95° C. After a 2 hour reaction time, the solution was clear, and after 6 hours no more epoxide was present. Lastly, 19.72 g (0.2 mole) of 37% HCl was added. The clear, yellowish solution contained 98.9% of the theoretically possible quantity of quaternary ammonium salt.

EXAMPLE 3

To 92.6 g (0.5 mole) of dimethyldecylamine (amine number 301.6), 609 g of water was added, and while stirring and cooling with tap water, 39.41 g (0.4 mole) of 37% HCl was added. 94.34 G (0.5 mole) of 1,2-epoxydodecane (epoxide number 8.48) was then added, and the solution was heated for 4 hours at 95° C., after which no epoxide was present in the solution. 9.85 G (0.1 mole) of 37% HCl was added and a yellowish, clear gel was obtained. The conversion to quaternary ammonium compound was complete for all practical purposes.

Similar results were obtained under similar conditions when instead of the dimethyldecylamine used in this Example 3, methyl-2-hydroxydodecylethanolamine, dimethylcoconutalkylamine, dimethyltallowalkylamine, diethyltallowalkylamine, or another tertiary amine with a fatty alkyl radical was employed.

What is claimed is:

1. A process for the manufacture of a quaternary ammonium compound comprising the steps of:
    (a) reacting in the presence of water a tertiary amine which is from about 50 to about 90 mole percent in the form of a salt of an inorganic or organic acid with a compound containing a terminal epoxy group to form a quaternary ammonium compound, wherein the compound containing a terminal epoxy group is selected from the group consisting of
    (i) a compound of the formula

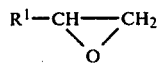  (I)

wherein $R^1$ is a straight or branched chain aliphatic hydrocarbon group having 1 to 21 carbon atoms or a group of the formula

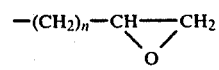  (II)

wherein n is an integer of from 4 to 16, and
    (ii) a compound of the formula

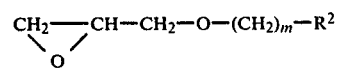  (III)

wherein m is an integer of from 1 to 10, and $R^2$ is hydrogen, or a straight or branched chain aliphatic hydrocarbon group having from 1 to 24 carbon atoms, or a group of the formula

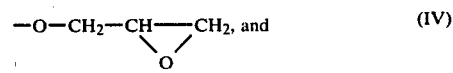  (IV)

wherein the tertiary amine contains at least one straight or branched chain alkyl, hydroxyalkyl or aralkyl group or an N-heterocyclic group containing the nitrogen atom of the tertiary amine in the ring structure, in which such group contains less than 10 carbon atoms; and
    (b) adding to the reaction mixture at the end of the reaction an inorganic acid, an acid salt, or an organic acid in an amount required for complete salt formation of the quaternary ammonium compound.

2. A process in accordance with claim 1 wherein first a tertiary amine is dissolved in water, an acid is added thereto to form an aqueous solution of a partial salt of the tertiary amine, and the compound containing a terminal epoxy group is added to the aqueous salt solution.

3. A process in accordance with claim 1 or 2 wherein the reaction is carried out at normal atmospheric pressure and at a temperature in the range of from about 40° to about 100° C.

4. A process in accordance with claim 3 wherein the reaction temperature is in the range of from about 80° to about 95° C.

5. A process in accordance with claim 1 or 2 wherein the tertiary amine partially in the form of a salt is formed by reacting one amine equivalent with from about 0.5 to about 0.9 equivalents of an inorganic acid, an acid salt, or an organic acid, and the reaction product therefrom is then reacted with one epoxide equivalent.

6. A process in accordance with claim 5 wherein from about 0.6 to about 0.8 equivalents of acid are present.

7. A process in accordance with claim 1 wherein $R^1$ in (a) (i) is an aliphatic hydrocarbon group having 4 to 16 carbon atoms.

8. A process in accordance with claim 1 wherein the epoxy compound contains from 10 to 20 carbon atoms.

9. A process in accordance with claim 1 or 8, wherein the tertiary amine and its salt contain an alkyl or alkenyl group having from 10 to 20 carbon atoms.

10. A process in accordance with claim 1 wherein the tertiary amine is from about 60 to about 80 mole percent in the form of a salt.

* * * * *